United States Patent
Fischer et al.

(10) Patent No.: US 7,268,882 B2
(45) Date of Patent: Sep. 11, 2007

(54) GAS SENSOR ARRANGEMENT IN AN INTEGRATED CONSTRUCTION

(75) Inventors: Joerg Fischer, Munich (DE); Marco Forlenza, Neuried (DE); Rudi Minuth, Freising (DE); Kuno Straub, Freising (DE); Thomas Tille, Munich (DE)

(73) Assignees: Tyco Electronics Raychem GmbH, Ottobrunn (DE); Bayerische Motoren Werke Aktiengesellschaft, Munich (DE)

( * ) Notice: Subject to any disclaimer, the term of this patent is extended or adjusted under 35 U.S.C. 154(b) by 408 days.

(21) Appl. No.: 11/058,893

(22) Filed: Feb. 16, 2005

(65) Prior Publication Data

US 2005/0259262 A1 Nov. 24, 2005

(30) Foreign Application Priority Data

Feb. 18, 2004 (DE) .................. 10 2004 007 946

(51) Int. Cl.
*G01N 21/00* (2006.01)
(52) U.S. Cl. .................. 356/437; 356/438; 250/343
(58) Field of Classification Search .............. 356/437, 356/438; 250/343
See application file for complete search history.

(56) References Cited

U.S. PATENT DOCUMENTS

| 5,127,729 A | * | 7/1992 | Oetliker et al. ............. 356/317 |
| 5,170,064 A | * | 12/1992 | Howe ......................... 250/343 |
| 5,767,967 A | * | 6/1998 | Yufa .......................... 356/336 |
| 5,973,326 A | * | 10/1999 | Parry et al. ................... 250/343 |
| 6,067,840 A | | 5/2000 | Chelvayohan et al. ......... 73/23.2 |
| 6,194,735 B1 | * | 2/2001 | Martin ........................ 250/437 |
| 6,410,918 B1 | | 6/2002 | Kouznetsov ................ 250/343 |
| 6,882,426 B1 | * | 4/2005 | Mueller ....................... 356/437 |
| 7,034,304 B2 | * | 4/2006 | Tice et al. ................... 250/343 |
| 2002/0139934 A1 | | 10/2002 | Chang ......................... 250/353 |

FOREIGN PATENT DOCUMENTS

| DE | 199 25 196 C2 | 12/2000 |
| EP | 53677 A1 * | 6/1982 |
| EP | 0 616 207 A2 | 9/1994 |
| WO | WO 00/55603 | 9/2000 |

OTHER PUBLICATIONS

European Search Report dated Jun. 10, 2005 for application No. EP 05 00 1208.

* cited by examiner

*Primary Examiner*—Hwa (Andrew) Lee
*Assistant Examiner*—Juan D Valentin, II
(74) *Attorney, Agent, or Firm*—Barley Snyder LLC

(57) ABSTRACT

A gas sensor arrangement comprises a first half-shell mateable with a second half-shell. The first half-shell has a detector receiving opening and radiation source receiving apertures. A gas measuring chamber is formed between the first half-shell and the second half-shell. The gas measuring chamber extends between the detector receiving opening and the radiation source receiving apertures. Concave mirrors are arranged around the radiation source receiving apertures. The concave mirrors are formed by inner surfaces of the first and second half-shells. Tubes extend from the concave mirrors to the detector receiving opening. The tubes are formed by the inner surfaces of the first and second half-shells. The inner surfaces are coated with a reflective material.

20 Claims, 5 Drawing Sheets

GAS SENSOR ARRANGEMENT IN AN INTEGRATED CONSTRUCTION

FIELD OF THE INVENTION

The invention relates to a gas sensor arrangement comprising at least one radiation source, a gas measuring chamber, and a radiation detector wherein the radiation detector generates an output signal dependant on the presence and/or concentration of an analyte in the gas measuring chamber.

BACKGROUND OF THE INVENTION

Gas sensor arrangements for detecting a wide variety of analytes, for example methane or carbon dioxide, are well known. Examples of such gas sensors are disclosed in EP 0616207 A2, WO 00/55603 A1, and DE 19925196 C2. The gas sensors comprise a radiation source, a gas measuring chamber, and a radiation detector. The gas sensors are based on the principle that a large number of polyatomic gases absorb radiation, particularly in an infrared wavelength range. The absorption occurs in a wavelength characteristic for the gas, for example at 4.24 µm for carbon dioxide. Using gas sensors, it is therefore possible to detect the existence of a gas component and/or the concentration of the gas component. The intensity of the radiation measured by the radiation detector is a measure of the concentration of the gas. Either a broadband radiation source may be used and the wavelength of interest adjusted via an interference filter or grid or a selective radiation source may be used, for example a light-emitting diode or a laser, in combination with non-wavelength-selective radiation receivers.

It is known from EP 0616207 A2 that bundling the radiation emitted from the radiation source increases the energy efficiency of the gas sensor. In order to bundle the emitted radiation, a concave mirror is positioned at a point at which the radiation detector is located and a metal funnel-shaped tube is arranged in front of the radiation detector so that the emitted radiation is focused onto a detection surface of the radiation detector.

In the motor vehicle sector, the detection of carbon dioxide is becoming increasingly important. For example, to increase energy efficiency during heating and air conditioning, the carbon dioxide content of the air in the interior of the vehicle is monitored. In the event that an increase in carbon dioxide concentration occurs, a supply of fresh air is introduced via a fan flap. Additionally, modern air conditioning systems are based on carbon dioxide coolants. The gas sensors can therefore fulfill a monitoring function in conjunction with issuing carbon dioxide in the event of potential defects. Gas sensors of this type, however, must meet stringent requirements with respect to ruggedness, reliability, and miniaturization.

SUMMARY OF THE INVENTION

It is therefore an object of the invention to provide an improved gas sensor arrangement that is energy efficient, robust, compact, and can be inexpensively produced.

This and other objects are achieved by a gas sensor arrangement comprising a first half-shell mateable with a second half-shell. The first half-shell has a detector receiving opening and radiation source receiving apertures. A gas measuring chamber is formed between the first half-shell and the second half-shell. The gas measuring chamber extends between the detector receiving opening and the radiation source receiving apertures. Concave mirrors are arranged around the radiation source receiving apertures. The concave mirrors are formed by inner surfaces of the first and second half-shells. Tubes extend from the concave mirrors to the detector receiving opening. The tubes are formed by the inner surfaces of the first and second half-shells. The inner surfaces are coated with a reflective material.

This and other objects are still further achieved by a gas sensor arrangement comprising a first half-shell and a second-half shell. The first half-shell is mounted on a printed circuit board and has a detector receiving opening and radiation source receiving apertures. The second-half shell is positioned over top of the first-half shell and is mounted on the printed circuit board. A gas measuring chamber is formed between the first half-shell and the second half-shell. The gas measuring chamber extends between the detector receiving opening and the radiation source receiving apertures. Concave mirrors are arranged around the radiation source receiving apertures. The concave mirrors are formed by inner surfaces of the first and second half-shells. Tubes extend from the concave mirrors to the detector receiving opening. The tubes are formed by the inner surfaces of the first and second half-shells. The inner surfaces are coated with a reflective material.

DETAILED DESCRIPTION OF THE INVENTION

Figure 1:
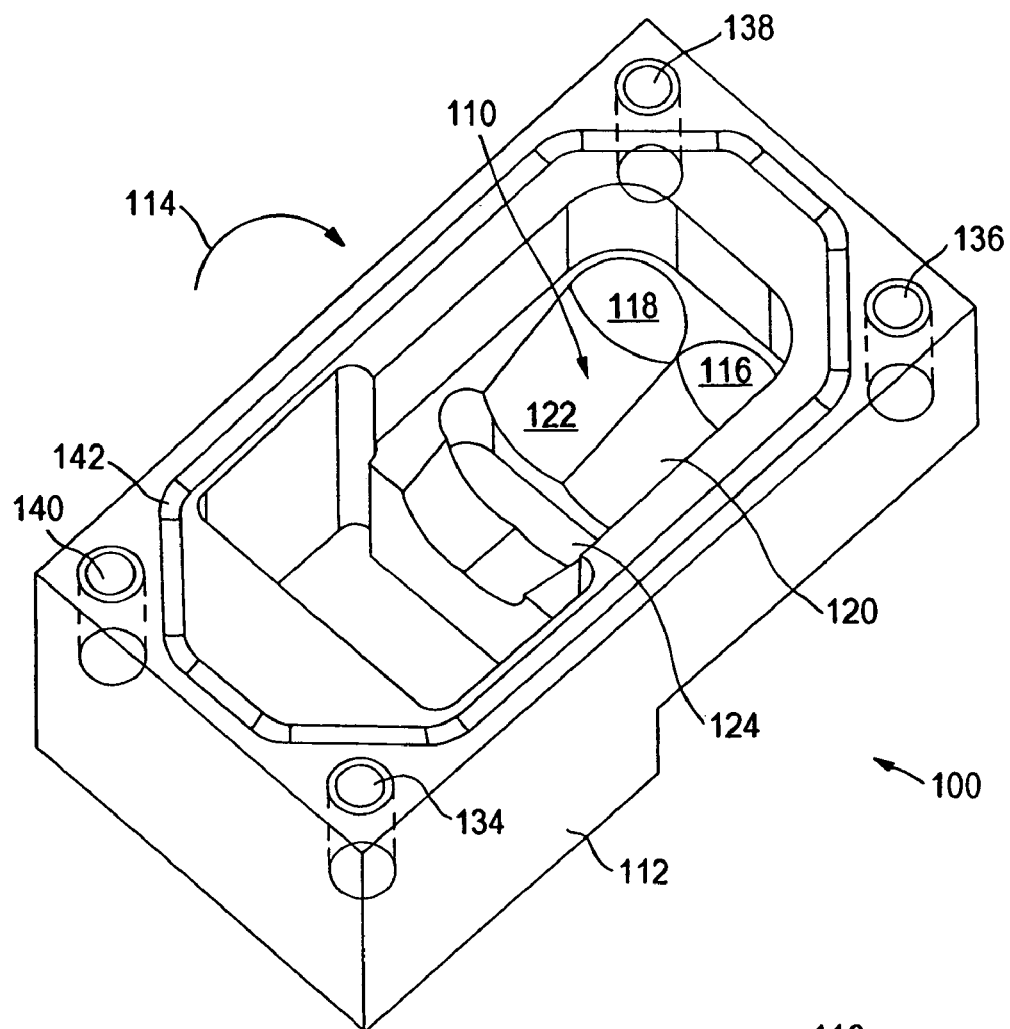
FIG. 1 is an exploded view of a gas sensor arrangement according to the invention.
Figure 1:
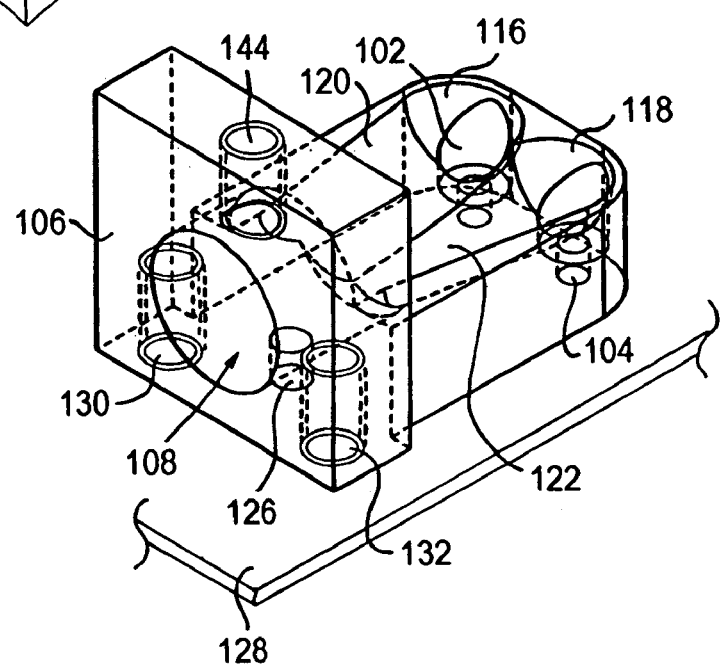
Figure 2:
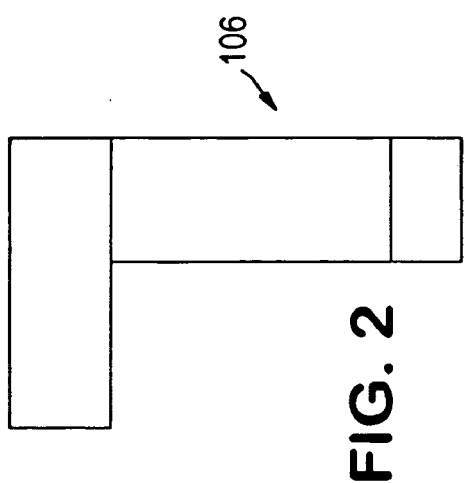
FIG. 2 is a side elevational view of a first half-shell.
Figure 3:
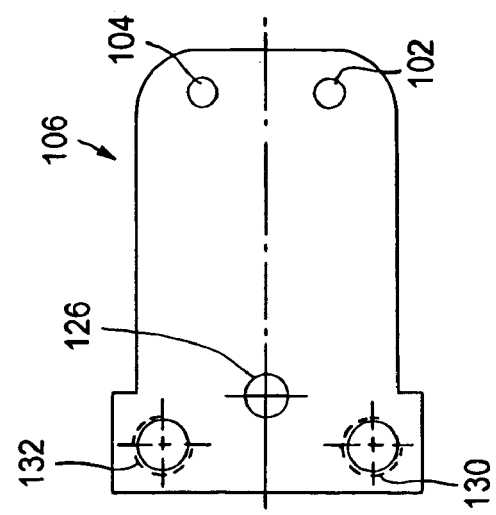
FIG. 3 is a bottom plan view of the first half-shell.

FIG. 1 shows a gas sensor arrangement 100 according to the invention. The gas sensor arrangement 100 comprises a housing including a first half-shell 106 and a second half-shell 112. The housing may be produced from a plastic material, for example by injection molding, so that the housing is inexpensive to manufacture and mechanically stable. As shown in FIGS. 1-3, the first half shell 106 has radiation sources (not shown) arranged in radiation source receiving openings 102, 104. The radiation sources may be, for example, lamps that emit a broadband light spectrum or light-emitting diodes (LEDs). The use of the LED primarily has the advantage that filter arrangements for selecting the wavelength may be dispensed with and therefore the arrangement can be further miniaturized and simplified.

Figure 4:
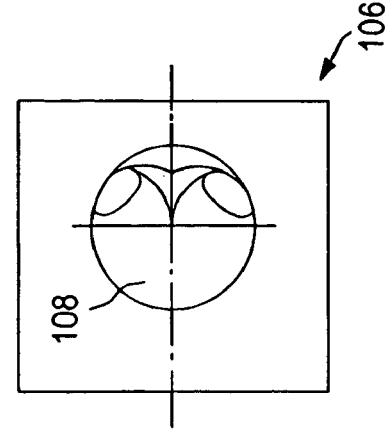
FIG. 4 is another side elevational view of the first half-shell.
Figure 7:
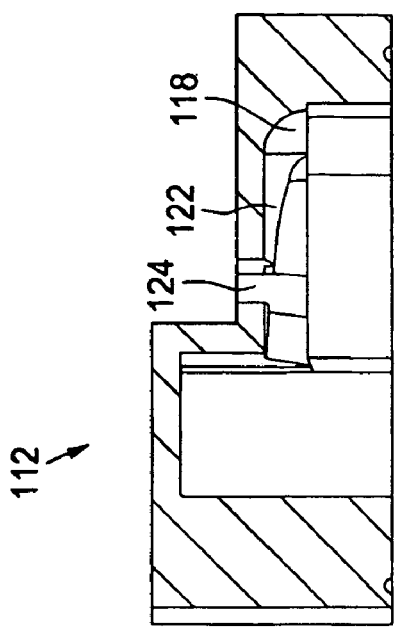
FIG. 7 is a sectional view taken along line A-A of FIG. 6.
Figure 8:
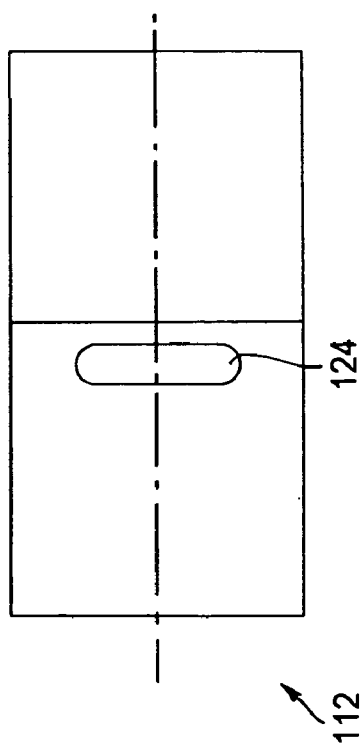
FIG. 8 is a top plan view of the second half-shell.

A detector (not shown) is arranged in a detector receiving opening 108 of the first half-shell 106, as shown in FIGS. 1 and 4. The detector (not shown) may be, for example, an infrared radiation detector that evaluates incident infrared radiation and supplies an electrical output signal as a function of the measured incident infrared radiation. The detector (not shown) is fixed to the first half-shell 106 by a screw (not shown) received in a threaded aperture 144. A gas measuring chamber 110 is formed when the second half shell 112 is slipped over the first half-shell 106 in a direction indicated by arrow 114 in FIG. 1. The gas measuring chamber 110 may be filled with a gas having at least one analyte via an elongated gas receiving aperture 124, as shown in FIGS. 7-8. The intensity of the incident infrared radiation on the detector (not shown) depends on the composition of the gas contained in the gas measuring chamber 110. To increase the accuracy of measurement, a temperature sensor (not shown) for monitoring temperature in the gas measuring chamber 110 may be introduced into the gas receiving chamber through a temperature sensor receiving opening 126. To prevent soiling and premature ageing of the gas sensor arrangement 100 the elongated gas receiving aperture 124 may be covered with a suitable filter material.

Concave mirrors 116, 118 are formed by coating inner surfaces of the first half-shell 106 and the second half-shell 112 with a reflective material, such as a gold layer. The reflective material may be a metal applied, for example, by sputtering, vapor deposition or electroplating. Each of the first and second half-shells 106, 112 contains approximately half of the concave mirrors 116, 118 such that a closed structure is formed by joining the first and second half-shells 106, 112. The concave mirrors 116, 118 are formed around the radiation sources (not shown). The concave mirrors 116, 118 are arranged in such a way that the radiation emitted by the radiation sources (not shown) is directed toward a detection surface (not shown) on the detector (not shown) by the concave mirrors 116, 118.

Cylindrical tubes 120, 122 are formed adjacent to the concave mirrors 116, 118 by the inner surfaces of the first half-shell 106 and the second half-shell 112. The tubes 120, 122 may have a funnel-shaped configuration. Each of the first and second half-shells 106, 112 contains approximately half of the tubes 120, 122 such that a closed structure is formed by joining the first and second half-shells 106, 112. The tubes 120, 122 are coated with the reflective material such that the tubes 120, 122 also convey the radiation emitted by the radiation sources (not shown) toward the detection surface (not shown) on the detector (not shown).

Figure 5:
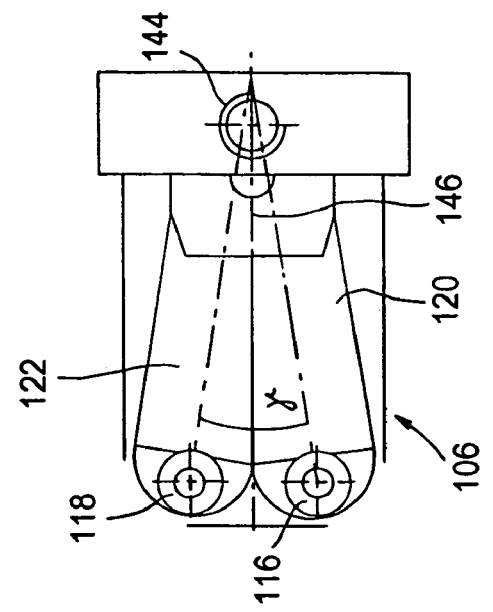
FIG. 5 is a top plan view of the first half-shell.
Figure 6:
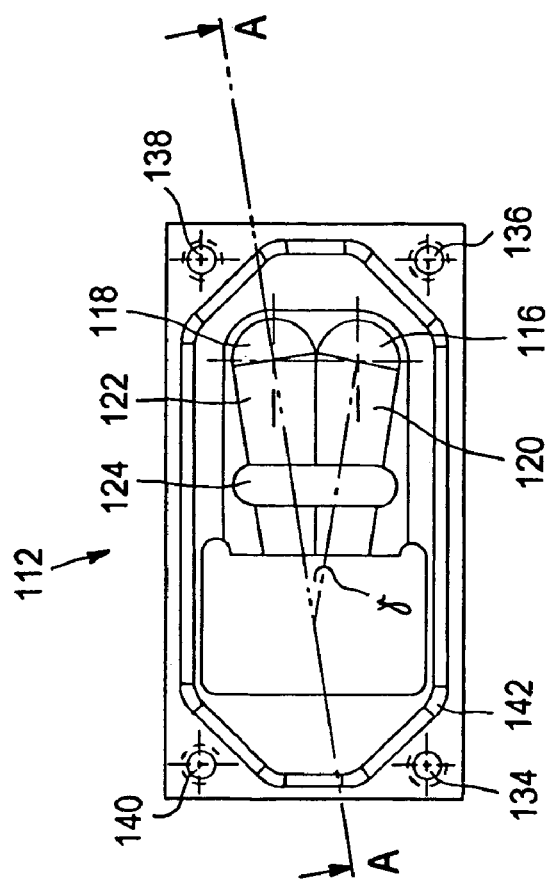
FIG. 6 is a bottom plan view of a second half-shell.

As shown in FIGS. 5-6, longitudinal axes of the tube 120 and the tube 122 enclose an angle γ, which is halved by an axis of symmetry 146 of the gas measuring chamber 110 such that the radiation is guided toward the detector (not shown). The radiation sources (not shown) are arranged symmetrically with respect to the axis of symmetry 146 of the gas measuring chamber 110 and the detector (not shown) is arranged on the axis of symmetry 146 in such a way that the radiation emitted from the radiation sources (not shown) are the same effective path length from the detector (not shown).

As shown in FIG. 1, the gas sensor arrangement 100 may be assembled as a complete module on a printed circuit board (PCB) 128. To mechanically fix the first half-shell 106 to the PCB 128, screws (not shown) are received in first half-shell mounting apertures 130, 132. The screws (not shown) are screwed into the PCB 128 to attach the first half-shell 106 thereto. Alternatively, a latching mechanism or the like may be used to attach the first half-shell 106 to the PCB 128. For fully automated assembly, the temperature sensor (not shown) and the radiation sources (not shown) could be arranged on the PCB 128 before the first half-shell 106 is attached thereto.

Figure 10:
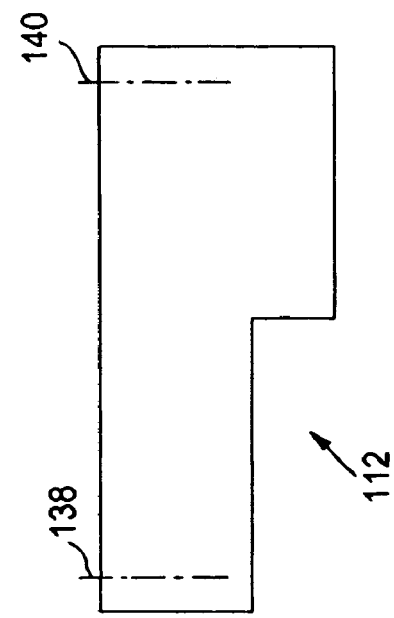
FIG. 10 is another side elevational view of the second half-shell.
Figure 9:
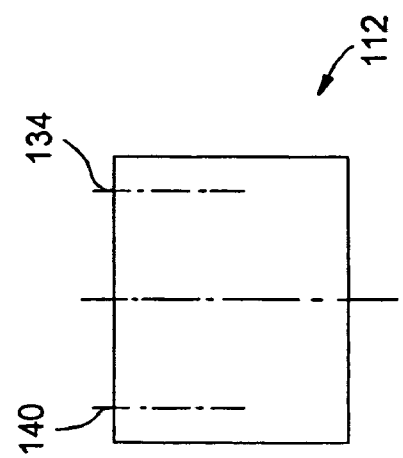
FIG. 9 is a side elevational view of the second half-shell.

After the detector (not shown) and radiation sources (not shown) are fixed in the first half-shell 106, the second half-shell 112 is fitted over the first half-shell 106 in the direction indicated by the arrow 114 in FIG. 1. The second half-shell 112 may be securely fixed to the PCB 128 by screws (not shown) received in second half-shell mounting apertures 134, 136, 138 and 140, as shown in FIGS. 1 and 9-10. A peripheral seal 142 that comes into contact with the PCB 128 may be provided on the second half-shell 112 to prevent moisture, dust, and disruptive stray light from entering the housing.

Figure 11:
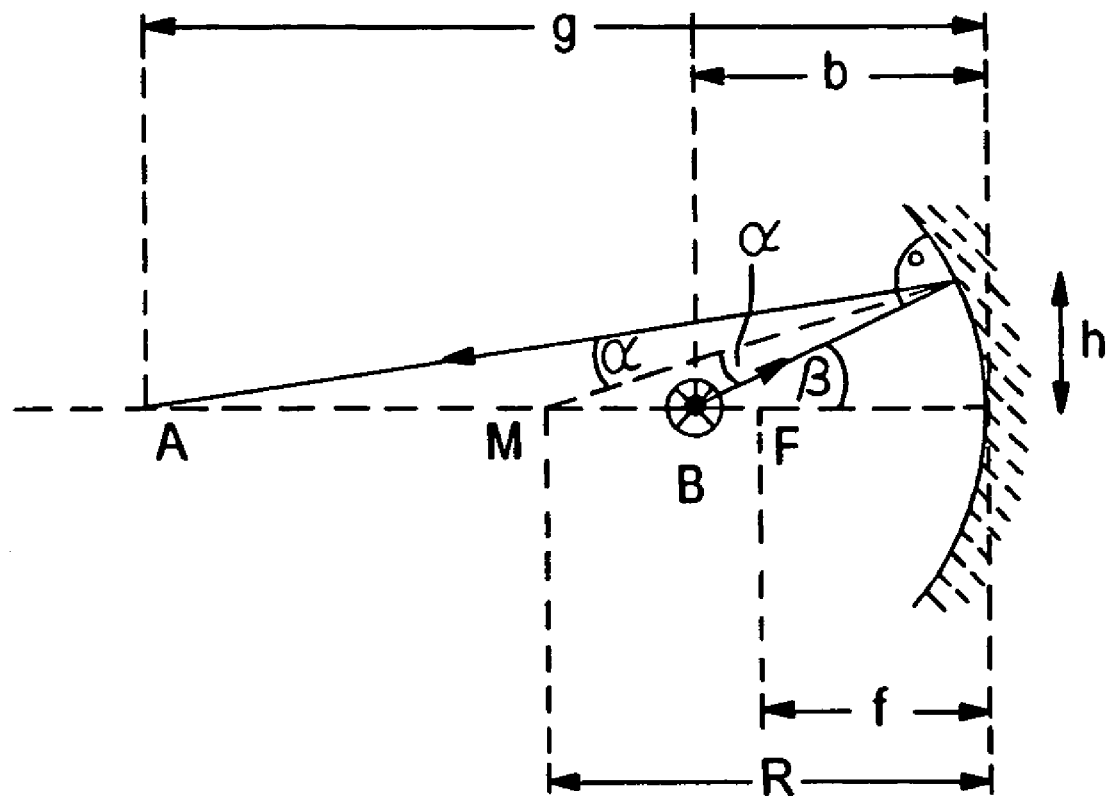
FIG. 11 is a schematic diagram for calculating dimensions of a concave mirror.

The geometric calculation of the concave mirrors 116, 118 will be discussed with reference to FIG. 11. As shown in FIG. 11, the radiation source (not shown) is arranged at point B for the best possible signal yield at the detector (not shown). The point B is in a vicinity of a focal point F of the concave mirror 116 and allows the radiation to be focused at point A, which corresponds to a position of the detector (not shown). The detector (not shown) has a detection surface (not shown) of about 1.5 millimeters squared. The concave mirror 116 has a center of curvature M and a radiation path angle 2α. Using the designations from FIG. 11, equations (1) and (2) apply:

$$1/f = 1/g + 1/b \qquad (1)$$

$$f = R/2 \qquad (2)$$

If the equation (1) is inserted into the equation (2) with the values 21.75 millimeters for g and 1.61 millimeters for b, the following is obtained for a radius R of the concave mirror:

$$R = \frac{2}{\frac{1}{21.75} + \frac{1}{1.61}} \text{ mm} = 3 \text{ mm} \qquad (3)$$

A height h is also selected as h=R=3 and angle β amounts to:

$$\beta = \frac{h}{g-k} = 9.16° \qquad (4)$$

The gas sensor arrangement 100 may be operated, for example, similar to DE 19925196 C2 wherein one of the radiation sources (not shown) is used as a measuring radiation source and the other of the radiation sources (not shown) is used as a reference radiation source. The reference radiation source may be switched on at intervals to check the age of the measuring radiation source. Deviations with respect to the output signals of the detector (not shown) when the reference radiation source and the measuring radiation source are switched on provide information about the age of the measuring radiation source, which can then be optionally compensated. Although in the illustrated embodiment, the gas sensor arrangement 100 uses a measuring radiation source and a reference radiation source, which are both focused on a single detector (not shown), the invention may also be used with a single radiation source or with more than the illustrated number of radiation sources and/or detectors.

The reliability and service life of the gas sensor arrangement 100, particularly in the motor vehicle sector, may therefore be fundamentally increased. Additionally, because the source receiving openings 102, 104, in which the radiation sources (not shown) are arranged, are located in the vicinity of the focal point of the concave mirrors 116, 118, the emitted radiation can be focused on the detection surface (not shown) of the detector (not shown). The metal coatings of the tubes 120, 122 also guide a portion of the radiation to the detector (not shown). Because the entire path followed by the emitted radiation is coated with a reflective metal coating, penetration of disruptive leakage radiation from outside of the housing is prevented.

Using the gas sensor arrangement 100 according to the invention, it is possible to optimize the signal yield at the detector (not shown) and simultaneously provide for highly simplified assembly which can be automated. The gas sensor arrangement 100 can be integrated into larger electronic systems in a particularly compact manner, because the gas sensor arrangement 100 is assembled as a module on the PCB 128. This arrangement also provides the advantage that a requisite electronic evaluation device (not shown), which further processes the output signal generated by the detector (not shown), can be constructed on the same PCB 128. The gas sensor arrangement 100 according to the invention can therefore be advantageously used in conjunction with motor vehicles that have limited space.

We claim:

1. A gas sensor arrangement, comprising:
    a first half-shell mateable with a second half-shell, the first half-shell having a detector receiving opening and radiation source receiving apertures;
    a gas measuring chamber formed between the first half-shell and the second half-shell, the gas measuring chamber extending between the detector receiving opening and the radiation source receiving apertures;
    concave mirrors arranged around the radiation source receiving apertures, the concave mirrors being formed by inner surfaces of the first and second half-shells;
    tubes extending from the concave mirrors to the detector receiving opening, the tubes being formed by the inner surfaces of the first and second half-shells; and
    the inner surfaces being coated with a reflective material.

2. The arrangement of claim 1, wherein the first-half shell has a temperature sensor receiving opening communicating with the gas measuring chamber.

3. The arrangement of claim 1, wherein the first half-shell is mounted to a printed circuit board.

4. The arrangement of claim 1, wherein the second-half shell is positioned over top of the first-half shell in a mated position.

5. The arrangement of claim 1, wherein the reflective material is gold.

6. The arrangement of claim 1, wherein the second half-shell has a gas receiving aperture communicating with the gas measuring chamber.

7. The arrangement of claim 1, wherein the tubes have a funnel-shape.

8. The arrangement of claim 1, wherein the radiation source receiving openings are arranged symmetrically with respect to an axis of symmetry of the gas measuring chamber.

9. The arrangement of claim 8, wherein the detector receiving opening is arranged on the axis of symmetry.

10. The arrangement of claim 1, further comprising a peripheral seal for sealing the gas receiving chamber.

11. The arrangement of claim 1, wherein the radiation source receiving openings are the same path length from the detector receiving opening.

12. A gas sensor arrangement, comprising:
    a first half-shell mounted on a printed circuit board, the first half-shell having a detector receiving opening and radiation source receiving apertures;
    a second-half shell positioned over top of the first-half shell, the second half shell being mounted on the printed circuit board;
    a gas measuring chamber formed between the first half-shell and the second half-shell, the gas measuring chamber extending between the detector receiving opening and the radiation source receiving apertures;
    concave mirrors arranged around the radiation source receiving apertures, the concave mirrors being formed by inner surfaces of the first and second half-shells;
    tubes extending from the concave mirrors to the detector receiving opening, the tubes being formed by the inner surfaces of the first and second half-shells; and
    the inner surfaces being coated with a reflective material.

13. The arrangement of claim 12, wherein the first-half shell has a temperature sensor receiving opening communicating with the gas measuring chamber.

14. The arrangement of claim 12, wherein the reflective material is gold.

15. The arrangement of claim 12, wherein the second half-shell has a gas receiving aperture communicating with the gas measuring chamber.

16. The arrangement of claim 12, wherein the tubes have a funnel-shape.

17. The arrangement of claim 12, wherein the radiation source receiving openings are arranged symmetrically with respect to an axis of symmetry of the gas measuring chamber.

18. The arrangement of claim 17, wherein the detector receiving opening is arranged on the axis of symmetry.

19. The arrangement of claim 12, further comprising a peripheral seal between the second half-shell and the printed circuit board.

20. The arrangement of claim 12, wherein the radiation source receiving openings are the same path length from the detector receiving opening.

* * * * *

UNITED STATES PATENT AND TRADEMARK OFFICE
CERTIFICATE OF CORRECTION

PATENT NO. : 7,268,882 B2
APPLICATION NO. : 11/058893
DATED : September 11, 2007
INVENTOR(S) : Fischer et al.

It is certified that error appears in the above-identified patent and that said Letters Patent is hereby corrected as shown below:

In claim 8, line 2, "openings" should read -- apertures--.

In claim 11, line 2, "openings" should read -- apertures--.

In claim 17, line 2, "openings" should read -- apertures--.

In claim 20, line 2, "openings" should read -- apertures--.

Signed and Sealed this

Fourth Day of December, 2007

JON W. DUDAS
*Director of the United States Patent and Trademark Office*